United States Patent [19]

Bickl et al.

[11] 4,082,465
[45] Apr. 4, 1978

[54] DETERMINATION OF EXTREME DENSITY VALUES OF PHOTOGRAPHIC ORIGINALS

[75] Inventors: Horst Bickl, Pullach; Helmut Treiber, Munich; Gunter Findeis, Sauerlach; Bernhard Knör; Bernd Payrhammer, both of Munich; Berthold Fergg, Taufkirchen, all of Germany

[73] Assignee: AGFA-Gevaert, A.G., Leverkusen, Germany

[21] Appl. No.: 790,136

[22] Filed: Apr. 22, 1977

Related U.S. Application Data

[63] Continuation of Ser. No. 616,399, Sep. 24, 1975, abandoned.

[30] Foreign Application Priority Data

Sep. 25, 1974 Germany ............................ 2445831

[51] Int. Cl.² .................... G01N 21/22; G01J 3/46
[52] U.S. Cl. .................... 356/203; 250/571; 356/175
[58] Field of Search ............... 356/175, 203; 250/559, 250/563, 571, 572

[56] References Cited

U.S. PATENT DOCUMENTS

| 3,034,400 | 5/1962 | Biedermann et al. | 356/203 |
| 3,435,243 | 3/1969 | Webb | 356/175 |
| 3,527,540 | 9/1970 | Bowker et al. | 356/175 |
| 3,768,913 | 10/1973 | Klimecki | 356/203 |

Primary Examiner—Vincent P. McGraw
Attorney, Agent, or Firm—Michael J. Striker

[57] ABSTRACT

Each original in a strip of such originals is scanned during longitudinal travel of the strip using a scanning spot which repeatedly traverses a stationary scan line extending transverse to the direction of strip travel. The scanning spot has a scanning speed such that the scanning spot travels from one to the other end of the stationary scan line in a time less than the time in which the strip travels a distance equal to the breadth of the scan line. The scanning spot which repeatedly traverses the scan line is generated using a light shield having a slit which delimits the scan line and a rotating disk having equiangularly spaced apertures which move through a stationary light beam passing through the moving strip of originals.

7 Claims, 3 Drawing Figures

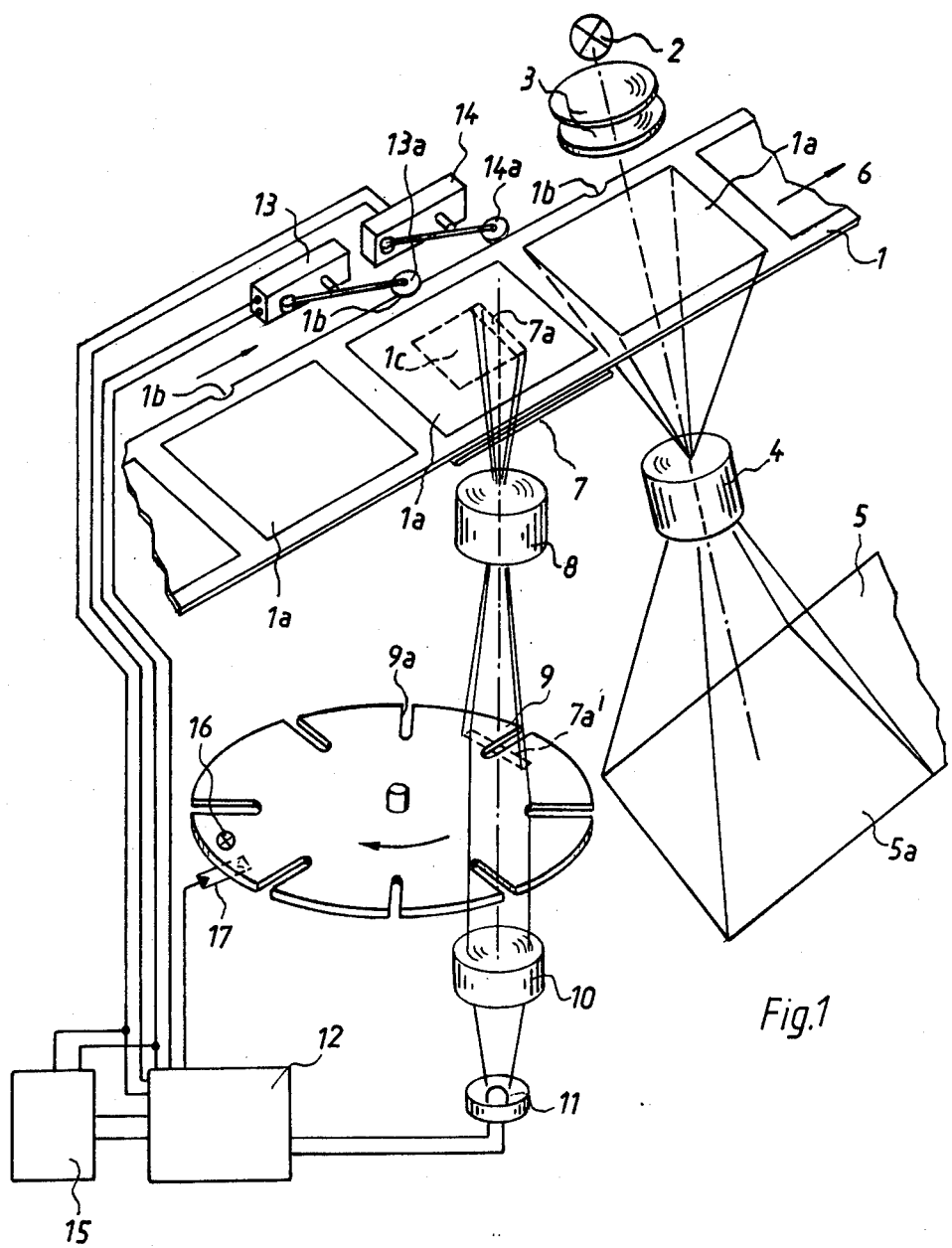
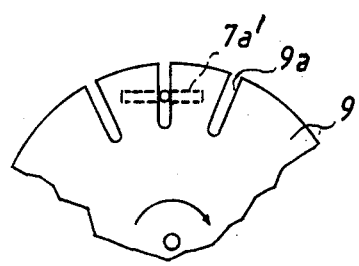
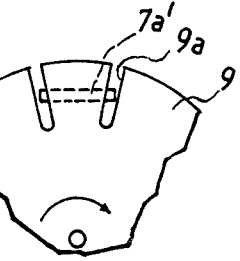
Fig.1
Fig.2
Fig.3
HORST BICKL
HELMUT TREIBER
GÜNTER FINDEIS
BERNHARD KNÖR
BERND PAYRHAMMER
BERTHOLD FERGG

DETERMINATION OF EXTREME DENSITY VALUES OF PHOTOGRAPHIC ORIGINALS

This is a continuation of application Ser. No. 616,399, filed Sept. 24, 1975, now abandoned.

BACKGROUND OF THE INVENTION

The invention relates to an arrangement for determining the extreme values from the density values in a plurality of individually scanned small scanned points of predetermined size in a certain section of a photographic original forming part of a strip of such originals. More specifically, the invention relates to the type of scanning arrangement which, for example, includes an objective projecting the image of the original, a rotating apertured disk located in an intermediate plane such that the apertures move through a stationary beam of light passing through the strip, a photoelectric transducer positioned behind the apertured disk to receive the light from a scanning spot formed by the apertured disk and generating a corresponding density-indicating electrical signal, and an evaluating arrangement for determining the extreme values of the electrical signal.

Federal Republic of Germany Pat. No. 1,070,492, and corresponding U.S. Pat. No. 3,034,400, disclose an exposure control arrangement provided with means for measuring the range of density values of each original to be printed. This is accomplished by using a semitransmissive mirror to extract from the main exposure light beam a supplemental beam which is passed through a Nipkow disk arranged in front of a photoelectric transducer. In this way, all points on the original to be copied are scanned one after the other and the density of such points measured by the photoelectric transducer. A complex electric circuit receives the signal from the photoelectric transducer and determines the minimum and maximum densities of the original to be copied, and also the range of density values of the original.

With this known arrangement the scanning is preformed while the original to be printed, and accordingly the strip of which the original forms one unit, is at a standstill. The scanning spot must be moved over the entire original, or the fraction thereof to be scanned, travelling both from side to side in the traversal of one scan line and top to bottom in moving from one scan line to the next. This scanning is performed either before or during printing of the original, with the measuring light beam for the scanning spot in part coinciding with the copying light beam for the printing operation. If the scanning is performed during the actual printing exposure, then the scanning must be completed before the end of the exposure time, and the exposure time may be very short for certain originals to be copied. As a result, if it should happen that the proper or correct exposure time has a certain minimum value, then the exposure will be undesirably prolonged because the scanning will continue until the completion of the scanning cycle to yield the density-range information ordinarily necessary to determine the duration (and/or intensity) of the printing exposure. The use of a separate photoelectric scanning means which does not derive its scanning light from the exposure light beam, in conjunction with an intermittent transport of the originals to be copied, gives rise to the problem that in the scanning station each original must be brought to a stop at a position corresponding very exactly to the position in the copying station.

SUMMARY OF THE INVENTION

It is a general object of the invention to devise a way of scanning the originals in a strip of photographic originals which does not necessitate careful positioning of the originals for scanning.

This object, and others which will become more understandable from the description, below, of preferred embodiments, can be met, according to one advantageous concept of the invention, by scanning each original during longitudinal travel of the strip using a scanning spot which repeatedly traverses a stationary scan line extending transverse to the direction of strip travel and has a scanning speed such that the scanning spot travels from one to the other end of the stationary scan line in a time less than the time in which the strip travels a distance equal to the breadth of the scan line.

Advantageously, the apparatus used to perform the method includes transport means for transporting the strip in a predetermined travel direction along a predetermined travel path, electromechanical scanning means operative for scanning each original in direction transverse to said travel direction during travel of the original in said direction using a scanning spot of substantially constant surface area and generating a corresponding electrical signal having a density-dependent value, and evaluating means for receiving the signal and determining extreme values of the signal.

Preferably, the electromechanical scanning means comprises a light source for alluminating the original being scanned, a photoelectric transducer positioned to receive light transmitted from the illuminated original, and beam-shaping means intercepting the path of the light for determining the shape of the scanning spot.

Advantageously, the beam-shaping means includes a stationary light shield positioned in the path of light from the light source and having a slit extending in direction transverse to the strip travel direction for establishing the limits of a scan line to be traversed by the scanning spot, and a rotating disk provided with apertures which during rotation of the disk move through the light from the source to define a scanning spot which travels along the scan line delimited by the slit. The apertures are perferably of equal angular breadth measured relative to the rotation axis of the rotating disk and are preferably equiangularly spaced from one another.

In scanning each original during the strip transport operation, all the portions of an original to be scanned pass one after the other under the scanning slit. Accordingly, these portions can be successively scanned in the region not covered by the transversely passing openings. In this way, the actual transport speed of the strip of photographic originals plays no role in the determination of the extrmeme values of density of the originals, so long as the strip transport speed is kept below a certain limit value. This limit value is the speed at which the strip is transported a distance equal to the breadth of the scan line in exactly the time required for the scanning spot to transverse the full length of the scan line.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 1 is a schematic representation of an inventive scanning arrangement;

FIG. 2 is an enlarged view of a portion of the structure shown in FIG. 1, during one phase of a scanning cycle; and FIG. 3 is a view like FIG. 2, during another phase of the scanning cycle.

DESCRIPTION OF THE PREFERRED EMBODIMENTS

In FIG. 1 reference numeral 1 designates a strip of photographic originals to be copied or printed, with numeral 1a denoting the surface area and positions of the originals themselves. Associated with each original there is provided at the upper lateral edge of the strip a respective notch 1b, arranged centrally with respect to the associated original. By means of the notch 1b, the associated original can be positioned in the copying or printing station. These notches can for example have been provided on the strip 1 by a specially designed scanning device operating in response to detection of the image frame 1a or the edges thereof. Instead of the notches, use could be made of perforations provided on the film before the film has been exposed and additionally utilized to properly position the film in the camera for picture taking.

In FIG. 1, the rightmost original 1a is located at a schematically depicted printing station comprised of a light source 2, a condenser lens system 3 and an objective 4 operative for focussing an image of the original 1a onto a strip 5 of light-sensitive material. An' exposure control arrangement is automatically operative for limiting the duration of the printing exposure in correspondence to the transmittance of the original 1a. Such an exposure control arrangement is disclosed for example in Federal Republic of Germany Pat. No. 1,070,492 and in corresponding U.S. Pat. No. 3,034,400, the entire disclosures of which are incorporated herein by reference. The printing station and the exposure control arrangement for terminating the exposure operation could take other forms, however.

Immediately upstream of the printing station, the strip 1, in travelling in the direction of arrow 6, passes through a scanning station in which extreme density values within the entirety of each individual original, or within a preselected limited scan region 1c of such original, are determined. For illuminating the original 1a present at the scanning station there is provided a light source and cooperating condensor lens system like the source 2 and system 3 of the copying station; to avoid crowding of the illustration, the light source and condenser of the printing station are omitted, but the downwardly travelling light therefrom is depicted.

There is provided at the scanning station, immediately below the film strip 1, a stationary light shield 7 having a narrow scanning slit 7a which extends in direction transverse to the strip travel direction 6. The scanning slit 7a delimits a scan line whose length corresponds to the breadth of the region 1c to be scanned and whose breadth corresponds to the breadth of the scanning spot which traverses this scan line. The evaluation of density will be the more exact, the smaller is the scanning spot; however, in general it will not be meaningful to make the scanning spot smaller than 1 × 1 mm. The breadth of the scan-line-delimiting slit 7a is for example approximately 1 mm for the film having a 24 × 36 mm format.

The section 1c of the original 1a is focussed by an objective 8 onto an intermediate plane in which is arranged a rotating slotted disk 9. The disk 9 is provided with slots 9a which are oriented generally radially and have a breadth corresponding to the breadth of the image 7a' of slit 7a as focussed onto the intermediate plane in which disk 9 lies. Accordingly, when the image 7a' of the slit 7a in the intermediate plane intersects one of the radial slots 9a perpendicularly, the slit 7a and the intersected slot 9a will together define the shape of a quadratic scanning spot. A beam of quadratic cross-section will pass through this zone of intersection and be focussed by a further objective 10 onto the photosensitive surface of a photoelectric transducer 11. Reference is made to a scanning spot, despite the fact that the light passing through the scanned portion 1c has the cross-sectional shape of the slit 7a; it will be clear that because such light must pass through the plane of the slotted disk 9 the only portion of the scanning beam which actually participates in scanning is a portion corresponding to a scanning spot on the original 1a. The scanning spot has a shape corresponding to the shape of the zone formed by the intersection of the image 7a' of slit 7a and one of the slots 9a.

The rotating disk 9 is driven at constant rotary speed by a non-illustrated electromotor. This speed is such that, if the film strip 1 travels at the highest foreseeable speed, the strip 1 will travel a distance less than the breadth of the scanning line defined by slit 7a during the time in which the disk 9 rotates through an angle equal to the spacing between successive slots 9a.

The slots 9a are equiangularly spaced. The slots 9a are so dimensioned and/or the offset between the disk rotation axis and the optical axis of objectives 8 and 10 is so selected that the length of the image 7a' of the slit 7a in the plane of the slotted disk 9 extends from the middle of one slot 9a to the middle of the next such slot (see FIGS. 2 and 3). Additionally, the rotation axis of disk 9 penetrates the plane of the film strip 1 at the connecting line between the midpoints of successive scanning sections 1c. The signal generated by the photoelectric transducer 11 is applied to a per se conventional evaluating arrangement 12.

The evaluating arrangement 12 compares each new value of the density-indicating signal with the previously registered value; if the new value is lower than the previously registered value, arrangement 12 continues to register the previous value, but if the new value is higher then the new value is registered. In this way the evaluating arrangement determines one extreme (maximum or minimum) of the density-indicating signal. In like manner, the evaluating arrangement determines the other extreme (minimum or maximum) of the density-indicating signal. Under certain circumstances, only one of the two extreme values may be determined.

For determining the moment at which a complete scanning cycle is to be initiated, there is provided alongside the edge of the film strip 1 a first sensing arrangement 13 for sensing the notches 1b. The sensing arrangement 13 includes a sensing roller 13a which briefly engages a passing notch 16 and thereby briefly interrupts an electrical circuit, to generate a timing signal. This timing signal is applied to the evaluating arrangement 12, causing the maximum and/or minimum signals registered during the previous scanning cycle to be erased. The evaluating arrangement 12 may for example be essentially comprised of a capacitor-charging circuit in which the capacitor voltage constitutes the registered extreme-value signal, with the value of this signal changing only if the voltage applied to the input of the circuit is higher than the capacitor voltage and thereby capable of further charging the capacitor. Accordingly, the extinguishing of the previously registered signal upon receipt of the timing signal from sensing arrangement 13 need only involve the brief activation of an electronic switch connected to discharge the capacitor, readying the arrangement to receive the density-indicating signal associated with the next original to be scanned.

A further sensing arrangement 14, of similar construction, is provided with a sensing roller 14a shifted relative to the roller 13a by a distance equal to the length of the scanning region 1c, as measured in the direction of arrow 6. Sensing arrangement 14 generates a timing signal when the scanning cycle is to be considered terminated. This timing signal, likewise, is applied to the evaluating arrangement 12 and effects the transfer of the extreme-value signal or signals registered by evaluating arrangement 12 to an exposure control arrangement 15. The control of this transfer can simply involve a gating circuit which directly transmits the registered signals from evaluating arrangement 12 to exposure control arrangement 15 during the brief time of the reception of the aforementioned timing signal. The exposure control arrangement 15 is operative in a per se known manner for controlling the duration of the printing or copying exposure for the original in dependence upon the maximum and/or minimum density values detected for such original. This can be performed, for example, by controlling a shutter to terminate the exposure operation at the proper instant.

The operation of the illustrated arrangement is as follows:

A film strip 1 is fed into the printing arrangement in the direction of arrow 6. The transport of the first notch 1b past the sensing arrangement 13 need not trigger a transport interruption; instead it is sufficient that scanning of the section 1c of the first original in the film strip 1 occur, and that the density-indicating signal derived during the scanning operation be applied to the evaluating arrangement 12.

The quadratic scanning spot determined by the edges of the slit 7a and of the slot 9a moves continuously with the peripheral speed of disk 9 along the length of the scanning line defined by slit 7a, covering that transverse strip of the section 1c which passes through the slit 7a during the transverse movement of the scanning spot. As the next such transverse strip of the section 1c enters into the region of the slit 7a, and the scanning spot disappears at one end of the scanning line, the scanning spot reappears at the other end of the scanning line, as shown in FIG. 3. For a brief time a part of a scanning spot will be present at both ends of the scanning line. As a result of the focussing of the pupil of objective 8 by objective 10 onto the photoelectric transducer 11, this has substantially the same effect as if both scanning beam sections emanated from a single area of approximately equal size. However, it is important that the surface area being scanned at any given instant be always at least approximately the same. This gives rise to certain restrictions: if only the maximum density is to be determined, then it suffices that the surface area scanned during the just-described transitional interval not be smaller than the nominal surface area of the scanning spot, because otherwise the indicated density could become great enough to unjustifiably supplant the previously registered maximum density value. Accordingly, the surface area scanned during the transitional interval should be if not equal to the nomal value then greater. On the other hand, if only the minimum density is to be determined, i.e., the transparency of the original at the most transparent point thereof, then the surface area scanned during the aforedescribed transitional interval should be if not equal to then smaller than the nominal surface area of the scanning spot. If both the minimum and maximum density are to be determined, then it is important to maintain with exactness the relationship between, on the one hand, the distance between the midpoints of successive slots 9a and, on the other hand, the length of the projected image 7a' of the slit 7a. This may for example involve adjustments which can be performed by shifting the rotation axis of disk 9 in the direction of the arrow 6.

Additionally, the angle intersected by the image 7a' of the slit 7a, on the one hand, and the slot 9a involved in the scanning at any given moment, on the other hand, should not deviate substantially from a right angle—i.e., it should not deviate from 90° by an amount greater than 10°—because the parallelogram resulting from non-perpendicular intersection has a surface area enlarged, relative to that of the original quadrilateral, by an amount corresponding to the reciprocal of the cosine of the intersection angle. If the deviation from perpendicular is kept to within 5°, the resulting change of scanning-spot surface area is completely negligible; if it is kept to within 10°, it is just tolerable. In this connection, it is to be noted that a section of the slit 7a lying further outside is focussed by the objective with rays of greater inclination, so that the peripheral loss of the objective at least partially compensates for the increased surface area of the scanning spot.

The transitional intervals, during which scanning spots disappear at one end of the scanning line and reappear at the other end of the scanning line, occur with regularity, at predetermined angular positions of the slotted disk 9. Accordingly, another way of counteracting the effect of the variation in scanning-spot surface area during such transitional periods involves blocking transmission of the density-indicating signal to the evaluation means during such transitional intervals. This can be done using photoelectric detector 16, 17 to detect the moments at which the slots 9 assume positions corresponding to transitional intervals. The signals generated at such moments by photoelectric detector 16, 17 can then be applied to a normally enabled gate, in the input circuit of evaluating arrangement 12, for briefly disabling the input gate, to prevent reception of the density-indicating signal during the transitional intervals. The effective shortening of the scan line can be compensated for by simply making the slit 7a somewhat longer.

When one of the notches 1b reaches a point corresponding to the proper position for an original at the printing station, the transport of the film strip 1 is briefly stopped, so that the printing operation can be performed. At such moment, the scanning of the selected section 1c of the original now located at the printing station will have already been completed and the minimum and/or maximum density value will have already been determined and fed into the automatic exposure control arrangement 15 for determining the control of the exposure shutter. By the time the notch 1b is sensed by the sensing arrangement 14, the extreme value or values registered by the evaluating arrangement 12 will have already been transferred into the exposure control arrangement 13 and erased from the evaluating arrangement 12, so that the evaluating arrangement 12 will be ready for the next scanning cycle.

When the scanning is performed in this way, there is no particular disadvantage in the fact that the transport speed of the film strip 1 may not be constant and that indeed it will change very markedly during the course of a single scanning operation. The only effect of such transport speed variations—provided of course that the aforedescribed relationship between the transport speed and the scanning speed is maintained—is that the scan lines actually traced on the moving original will be packed more densely together, i.e., adjoining scan lines actually traced on the moving original will be offset a distance smaller than their breadth, so as to overlap. This only serves to increase the accuracy of the evaluation dependent upon the scanning operation, without in any way increasing the cost of the arrangement or its operation.

The invention is not limited to the illustrated version just described. For example, the focussing optics for projecting the image of the scan-line-delimiting slit onto the photoelectric transducer could be differently designed; for example, a photoelectric transducer having a larger photosensitive surface could be arranged immediately beneath the slotted disk 9. Likewise, the slitted light shield 7 and the disk 9 could be arranged immediately adjacent each other. The synchronization with the film strip transport can be performed by other known sensing means, for example known arrangements for measuring distance travelled. It is of significance that by sensing the notches 1b the spacing of the originals on the film strip 1 has no influence upon the results of the scanning and subsequent evaluation.

The definition of the shape of the scanning spot need not be performed jointly by two discrete members, namely the stationary light shield 7 and the rotating disk 9. Instead, the shape of the scanning spot could be completely determined by the rotation disk 9. The slit of the light shield 7 could then be arcuate and concentric with the rotation axis of disk 9, and the disk 9 could be provided with circular apertures instead of the radial slots 9a, with all the circular apertures being identically spaced from the rotation axis of the disk. Depending upon the radius of curvature of the arcuate slit, the scan region 1c of each original 1a actually scanned would be more or less distorted from the rectangular shape in the illustrated embodiment; however, if the scanning region 1c does not extend all the way to the edges of the original 1a, this makes no great difference. An advantage of having the shape of the scanning spot completely determined by the apertures in the rotating disk is that it becomes possible to assure a constant shape and size of the scanning spot. In this event, the slitted light shield only serves to establish the ends of the scan line. In principle the slitted light shield could then be omitted, with the ends of the scan line being determined electromechanically, e.g., using the photoelectric detector 16, 17, or the like, to effect blanking out of the density-indicating signal generated at the output of photoelectric transducer 11, in the manner already described. In principle it would be possible to employ a rotating disk having only a single scanning aperture. Also, in principle it would be possible to employ a non-rotating cyclically moving member, such as an oscillating member.

It will be understood that each of the elements described above, or two or more together, may also find a useful application in other types of constructions differing from the types described above.

While the invention has been illustrated and described as embodied in a particular scanning arrangement, it is not intended to be limited to the details shown, since various modifications and structural changes may be made without departing in any way from the spirit of the present invention.

Without further analysis, the foregoing will so fully reveal the gist of the present invention that others can be applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. In an apparatus for determining the extreme density values of the originals in a strip of photographic originals, of the type provided with evaluating means for receiving an electric signal having a value dependent upon the density of the originals and determining extreme values of the signal, in combination, transport means for transporting the strip in a predetermined travel direction along a predetermined travel path; and electromechanical scanning means operative for scanning each original in direction transverse to said travel direction during travel of the original in said direction using a scanning spot of substantially constant surface area and generating a corresponding electrical signal having a density-dependent value, said scanning means comprising a light source for illuminating the original being scanned, a photoelectric transducer positioned to receive light transmitted from the illuminated original, and beam-shaping means intercepting the path of the light for determining the shape of said scanning spot, said beam-shaping means including a stationary light shield positioned in the path of light from said light source and having a slit extending in direction transverse to said travel direction for establishing the limits of a scan line to be traversed by said scanning spot, and a rotating disk provided with apertures which during rotation of said disk move through the light from said source to define a scanning spot which travels along the scan line established by said slit, said apertures being of equal angular breadth measured relative to the rotation axis of said rotating disk and being equiangularly spaced from one another, the angular spacing between adjoining ones of the apertures of the rotating disk being such that during the transitional time interval at the end of a line scan operation when the scanning spot defined by one aperture reaches and begins to disappear into one end of the scan line the scanning spot defined by the next aperture simultaneously therewith begins to appear at the other end of the scan line, adjoining apertures of the rotating disk accordingly being operative for simultaneously transmitting to the photoelectric transducer the light transmitted through the two ends of the scan line during the transitional time interval, said scanning means comprising means for rotating said disk at such a speed that each scanning spot produced by one of said apertures of said rotating disk travels from one to the other end of said scan line within a time no greater than that in which the strip is transported a distance equal to the breadth of the scanning spot as measured in said travel direction of the strip.

2. The apparatus defined in claim 1, wherein said apertures of said rotating disk are radially extending slots, and wherein said slit of said stationary light shield defines immediately adjacent the travelling strip of photographic originals a scanning zone having a breadth measured in said travel direction corresponding to the breadth of said scan line.

3. The apparatus defined in claim 2, wherein said radially extending slots and said slit form an angle which differs from 90° by no more than 10° during the travel of said scanning spot from one to the other end of the scan line delimited by said slit.

4. The apparatus defined in claim 3, wherein each radially extending slot forms an angle of 90° with said slit when the scanning spot produced by such slot and said slit is intermediate the ends of the scan line delimited by said aperture.

5. The apparatus defined in claim 1, further including means for determining when scanning spots produced by said apertures enter and leave the scan line delimited by said slit for preventing evaluation of said electrical signal by said evaluating means at such times.

6. The apparatus defined in claim 1, further including means for detecting an indication on the strip of an original to be evaluated for initiating operation of said evaluating means and means for detecting when such indication has moved a certain distance corresponding to the length of the section of the original to be scanned for terminating operation of said evaluating means.

7. A method of scanning the successive originals in a strip of such originals during longitudinal travel of the strip in order to determine the extreme density values of the originals, comprising scanning each original during longitudinal travel of the strip using a scanning spot which repeatedly traverses a stationary scan line extending transverse to the direction of strip travel and has a scanning speed such that the scanning spot travels from one to the other end of the stationary scan line in a time less than the time in which the strip travels a distance equal to the breadth of the stationary scan line, the scanning spot when at the end of the scan line disappearing into the end of the scan line with a progressive decrease in cross-sectional area but simultaneously reappearing at the start of the scan line with a corresponding progressive increase in cross-sectional area, so that during the progressive disappearance of the scanning spot into the end of the scan line and simultaneous progressive reappearance of the scanning spot from out the start of the scan line the combined cross-sectional areas of the parts of the scanning spot at the end and at the start of the scan line will be substantially constant and substantially equal to the cross-sectional area which the scanning spot has when traversing the middle portion of the scan line.

* * * * *